(12) United States Patent
Fadler et al.

(10) Patent No.: US 7,725,166 B2
(45) Date of Patent: May 25, 2010

(54) IMAGE-ASSISTED SHOCKWAVE THERAPY INSTALLATION

(75) Inventors: Franz Fadler, Hetzles (DE); Rainer Kaltschmidt, Eckental (DE); Markus Lanski, Fürth (DE); Walter Polster, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 970 days.

(21) Appl. No.: 10/587,781

(22) PCT Filed: Feb. 17, 2005

(86) PCT No.: PCT/EP2005/050704

§ 371 (c)(1),
(2), (4) Date: Jul. 28, 2006

(87) PCT Pub. No.: WO2005/082261

PCT Pub. Date: Sep. 9, 2005

(65) Prior Publication Data

US 2007/0276297 A1 Nov. 29, 2007

(30) Foreign Application Priority Data

Mar. 1, 2004 (DE) .................. 10 2004 010 005

(51) Int. Cl.
*A61B 5/05* (2006.01)
*A61H 1/00* (2006.01)
(52) U.S. Cl. .......................... 600/427; 601/4
(58) Field of Classification Search ............... 600/427; 601/2–4
See application file for complete search history.

(56) References Cited

U.S. PATENT DOCUMENTS

| 5,044,354 A | 9/1991 | Goldhorn et al. |
| 5,065,741 A | 11/1991 | Uchiyama et al. |
| 5,070,861 A * | 12/1991 | Einars et al. .................. 601/4 |

(Continued)

FOREIGN PATENT DOCUMENTS

DE 298 24 080 U1 6/2000

(Continued)

OTHER PUBLICATIONS

Dornier MedTech Brochure for *Compact Delta* Electromagnetic Shockwave Emitter (2000).

(Continued)

*Primary Examiner*—Eric F Winakur
*Assistant Examiner*—Michael T Rozanski
(74) *Attorney, Agent, or Firm*—Schiff Hardin LLP

(57) ABSTRACT

An installation for image-assisted shockwave therapy has a C-arm x-ray unit that is orbitally movable around an isocenter, and that carries an x-ray imaging system thereon. The installation also has a shockwave head and a carrier device for the shockwave head that is disposed stationarily relative to the x-ray C-arm. A boom that extends toward the x-ray C-arm is carried by the carrier device, the boom having a free end at which the shockwave head is mounted. The boom is movably guided by the carrier device so that the shockwave head is arbitrarily movable to any position and can be arbitrarily aligned to the isocenter within a minimum range of 180° delimited by the top table position and the bottom table position of a patient table.

6 Claims, 6 Drawing Sheets

U.S. PATENT DOCUMENTS

| | | | |
|---|---|---|---|
| 5,703,922 A * | 12/1997 | Rattner | 378/65 |
| 7,493,155 B2 * | 2/2009 | Kaltschmidt et al. | 600/427 |
| 2001/0046184 A1 | 11/2001 | Reitter et al. | |
| 2003/0078523 A1 | 4/2003 | Burkhardt et al. | |

FOREIGN PATENT DOCUMENTS

| | | |
|---|---|---|
| DE | 102 36 177 A1 | 3/2004 |
| JP | 8-19183 | 7/1996 |

OTHER PUBLICATIONS

Storz Medical Brochure for Modulith® SLK Shockwave Therapy Station.

* cited by examiner

IMAGE-ASSISTED SHOCKWAVE THERAPY INSTALLATION

BACKGROUND OF THE INVENTION

1. Field of the Invention

The invention concerns a system for image-supported shockwave treatment

2. Description of the Prior Art

The main components of a system of the above type are a therapy system and an x-ray system. The therapy system includes a shockwave head that generates ultrasonic waves directed towards a focus point. The primary purpose of such a treatment is the disintegration of kidney and ureter stones. Other applications for treatment of Peyronie's disease or in the field of pain therapy and gastroenterology are also conceivable. The x-ray system serves for location of the stone in the treatment area of a patient and for observation of the treatment success accompanying therapy. It has an x-ray source and an x-ray receiver or image intensifier. Both devices are fixed on the ends of a c-shaped arc (called an x-ray C-arm in the following) that can move orbitally around its isocenter. In the application case the x-ray C-arm partially encompasses a patient table or is partially crossed by this in the direction of an axis running at a right angle to the orbital plane of said x-ray C-arm.

In the treatment of a patient with a system of the type illustrated above, the focus point of the shockwave head must be aligned on the isocenter of the x-ray C-arm or coincide therewith so that, given orbital or angular movement of the x-ray system required for 3D positioning, the beam axis of the x-ray system always proceeds through the focus point or through a volume region surrounding this focus point. In the application case, the therapy subject to be treated must correspondingly likewise be arranged in the aforementioned region, meaning that the patient must be suitably positioned on the patient table. In systems with stationary shockwave head, this requirement can only be satisfied by a position that is uncomfortable for the patient, for example by a prone position, which is particularly uncomfortable for adipose patients.

In a system known from DE 298 24 080 U1, a carrier device (fashioned as a C-arm) for a shockwave head is arranged in the orbital plane of an x-ray C-arm that can be only angularly moved. The C-arm has a first arc segment fixed on the x-ray C-arm and a second arc segment supported on the first fixed arc segment such that it can shift along this segment. The second arc segment carries the shockwave head on its free end. The first arc segment and the x-ray C-arm itself can be rotated around a common horizontal axis angularly running in the orbital plane and through the isocenter of the x-ray C-arm. Due to this embodiment, a shockwave head can be positioned both above and below a patient table. A disadvantage of this arrangement is that the space circumscribed by the x-ray C-arm is crowded by the carrier device such that a displacement of the patient table running horizontal and parallel to the orbital plane operating system is barely possible. Given a change from a left-side treatment position to a right-side treatment position, with an unchanged patient position, the patient volume therefore cannot be brought into the focus point or the isocenter via a table displacement. Rather, a head-to-foot rearrangement of the patient is necessary. The result is that the previous spatial orientation must be adapted to the new patient position; for example, a time-consuming reconstruction of auxiliary devices (such as anesthesia devices) must be effected.

SUMMARY OF THE INVENTION

An object of the invention to provide a system for shockwave treatment that is improved in this regard.

This object is achieved by a system according to the invention having an x-ray C-arm that can move orbitally around an isocenter and a carrier device for the shockwave head that is arranged stationary and axially offset relative to the x-ray C-arm. A boom extending up to the x-ray C-arm is connected with the carrier device with its fixed end and supports the shockwave head with its free end. With the carrier device, the boom is movably directed such that the shockwave head can be arbitrarily positioned in the orbital plane within an angle range of at least 180° above and below a patient table and can be aligned on the isocenter. Due to the axially-offset arrangement of the carrier device, the entire space enclosed by the x-ray C-arm is freely accessible. This allows a patient table to be horizontally displaced so that a treatment change from the right patient side to the left patient side (thus a positioning of the left-side or right-side treatment area of the patient in the isocenter) can ensue without having to effect a head-to-foot rearrangement. The original setup of the system can be retained, which is particularly advantageous when, for instance, a patient with kidney stones on both sides is treated. Due to the movement capability of the boom (and with it of the shockwave head) in an angle range of at least 180°, the latter can be arranged, for example, in an under-table position with vertical alignment of its shockwave axis (0° position) and in an over-table position with the same shockwave axes alignment (180° position). Given a movement range of 230°, a movement from the vertical over-table position (180°) up to a −50° position under the table can ensue. Nearly all treatment situations on a patient can be implemented with the patient in the same position. In the extreme case, the carrier device can be designed such that an angle range of 360° can be covered with the shockwave head. A large variability is thus available with regard to the selection of the treatment position of the shockwave head; for example, a ureter stone treatment can be effected from an over-table position or an under-table position given a dorsal position of the patient.

If the carrier device for the shockwave head is arranged in the head direction of the patient with regard to the x-ray C-arm, the doctor has free access to the patient up to the height of the point of the patient to be treated and from the foot region of the patient on the side facing towards the machine such that, for instance, a trans-urethral procedure is possible without hindrance. The inventive arrangement also provides sufficient freedom of movement for an anesthesiologist operating in the head region of the patient.

Due to the orbital movement capability of the x-ray C-arm, both the locating and the observation during the treatment (perhaps the progress of a stone disintegration) can ensue from the direction of the shockwave axis, which offers a higher targeted precision (inline positioning). Shadowing of the x-rays by a carrier structure for the shockwave head that is arranged within the x-ray C-arm thus is not a concern. Only the shockwave head itself is arranged within the volume range swept by the x-ray of the x-ray system. The boom that supports the shockwave head does not interfere, particularly when it holds the shockwave head from the side with its free end. In summary, according to the invention a system is provides that allows a shockwave treatment in arbitrary angle positions as well as from different intromission angles with an always-constant alignment and dorsal position of the patient, as well as the precisely-targeted x-ray inline positioning and a nearly hindrance-free observation with the x-ray system during the treatment. The system is therefore likewise suitable for a number of applications, for example IPP, kidney, ureter and bladder stones, trans-urethral procedures.

Because both sub-systems (namely the x-ray system and the therapy system) are stationary relative to one another, for example accommodated on a common base, their position relative to one another is mechanically fixed. For instance, given the mounting of the system an adjustment can ensue to cause the focus point of the shockwave head to be directed on the isocenter or to coincide therewith in every treatment position. For instance, the usage of an electronic positioning system for position establishment or calculation of the position of focus and isocenter is not necessary.

In a preferred embodiment the boom is forced to stay in a plane parallel to the orbital plane of the x-ray C-arm. A lateral existing of the focus point of the shockwave head from the orbital plane of the x-ray C-arm is thereby prevented.

Preferably, the carrier device is a C-arm (designated in the following as a therapy arc) arranged axially offset and coaxial relative to the x-ray C-arm, on which therapy arc C-arm the boom is supported with its fixed end such that the boom can move orbitally. This embodiment allows a complete guided movement of the shockwave head in the orbital plane of the x-ray C-arm. An adjustment of the focus point of the shockwave head to the isocenter of the x-ray C-arm, which adjustment is effected given the new installation of a system, is retained.

In the normal case, movement of the shockwave head around a specific angle range requires a therapy arc with an at least correspondingly-dimensioned arc length. Given a movement capability of the shockwave head, for example by 250°, a correspondingly-dimensioned therapy arm would significantly overlap a treatment table on the top and bottom and thereby limit the movement freedom of a treating doctor on the treatment side of the patient table. In order to prevent this, in an embodiment the therapy arc is supported such that it can be orbitally displaced. The therapy arc can then be significantly shortened since the maximum travel path of the shockwave head results from the travel length of the therapy arc and the travel length of the shockwave head on the therapy arc. To shorten the therapy arc length it is also conceivable to form this from two arc segments that can be orbitally displaced against one another. Another possibility for arc truncation is to affix the boom on the therapy arc such that the boom can rotate, such that its free end can be pivoted into a position protruding over a free end of the therapy arc.

In a second embodiment of the system, the carrier device is an articulated arm formed by a number of arm segments connected by joints, with fixed end of the boom connected to the free end of the articulated arm. While establishment of the movement of the boom or of the shockwave head in an orbit is determined by the therapy arc, the desired treatment positions of the shockwave head can be achieved with the use of an articulated arm as a carrier device with arbitrary movement paths, in which case a control device for isocentric alignment of the shockwave head is then required. In an embodiment the degree of freedom of the articulated arm is limited such that it can move only within a plane parallel to the orbital plane of the x-ray C-arm. This is achieved in an appropriate manner by the joints of the articulated arm connecting the arm segments exhibiting rotation axes proceeding parallel to one another and at right angles to the orbital plane of the x-ray C-arm, thus are all fashioned as hinge joints. In order to be able to isocentrically align the shockwave head in each angle position, the boom is rotatably connected with the free end of the articulated arm.

In both embodiments, the shockwave head is traversed (penetrated) by a central region that is permeable to x-rays and extends along the shockwave axis of the shockwave head. This embodiment allows a precisely targeted "inline positioning" with the x-ray system without position change of the shockwave head, thus also during a lithotripsy treatment. In a design that is likewise advantageous for both embodiments, the carrier device (together with the shockwave head) can be moved from a treatment position into a park position removed from a patient table or, a patient borne thereupon. The freedom of movement in the space located between x-ray C-arm and head end of the patient table or, respectively, generally in the abdominal region of the patient thus can be increased.

In order to not hinder orbital movement of the x-ray C-arm and of the therapy arc, or a movement of the articulated arm on the underside of the patient table, the arm is supported at one end, for example at the head end, thus outside of the movement range of the aforementioned devices.

DESCRIPTION OF THE PREFERRED EMBODIMENTS

Figure 1:
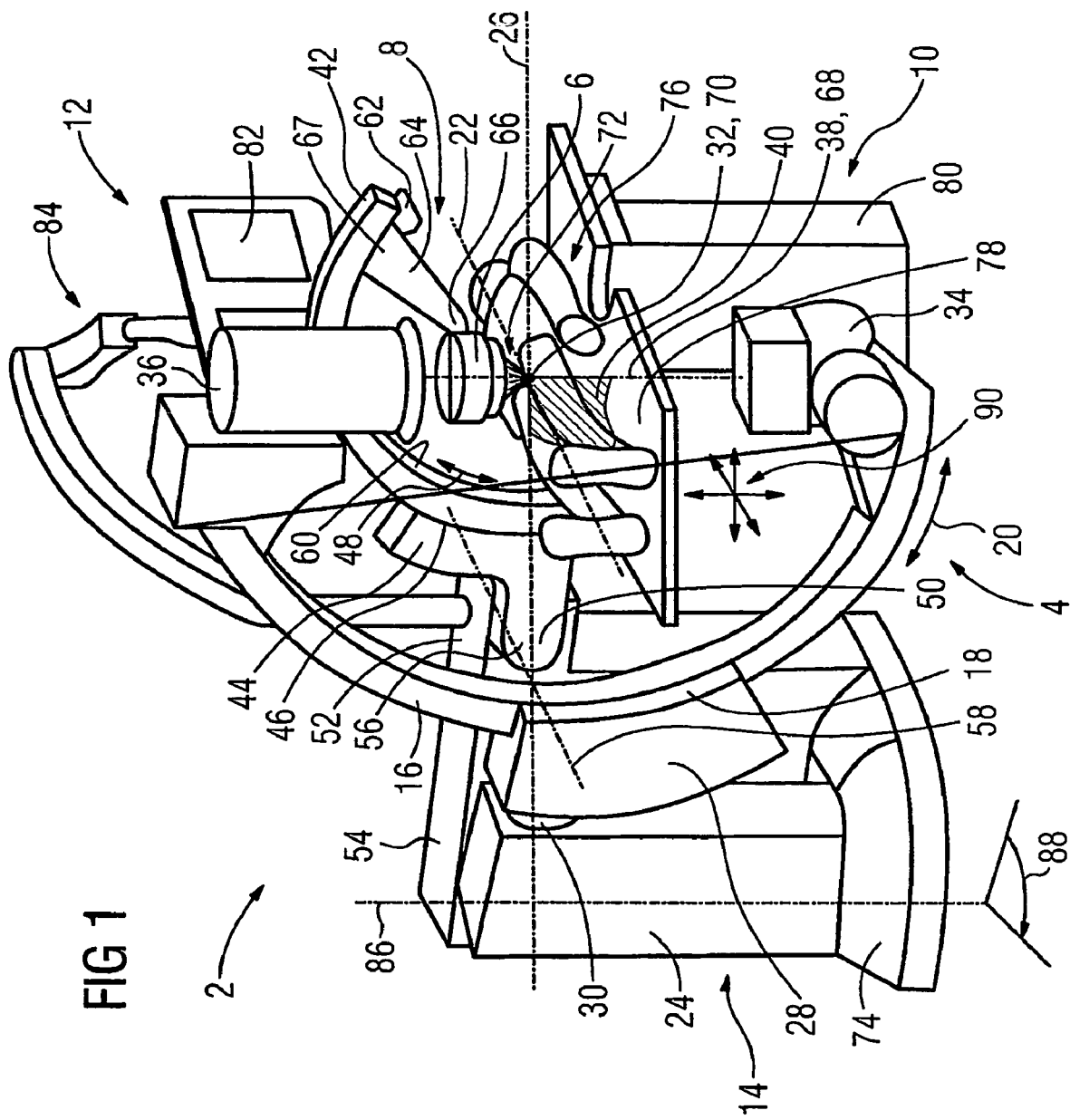
FIG. 1 shows a shockwave lithotripsy system in a first embodiment with shockwave head in the over-table treatment position and the x-ray C-arm in a base position (inline with the shockwave head).

FIG. 1 shows an SWL system 2 in a first embodiment that has the following sub-components: an x-ray C-arm 4, a therapy C-arm 8 (bearing a shockwave head 6 and characterizing the first embodiment) as a carrier device, a patient table 10 and a display module 12. The x-ray C-arm 4 has a two-part base body 14 on which a C-arm segment 16 is movably supported. A segment-shaped support 18 (not visible) is present in the base body 14 for this purpose, in which support 18 the C-arm segment 16 is forcibly guided, optimally without play. The C-arm segment 16 can therefore be moved one-dimensionally in the orbital direction indicated by the double arrow 20.

The two-part base body 14 has a base 24 that is stationary at rest. A guide 28 that can rotate around a pivot axis 26 proceeding horizontally is attached on this base 24 via a swivel joint 34. The pivot axis 26 intersects a longitudinal axis 22 at an isocenter 32. The x-ray C-arm 4 can be moved angularly around the pivot axis 26. The orbital movement of the C-arm segment 16 ensues around a longitudinal axis 22 proceeding horizontally given the angular base position shown in FIG. 1. Given angular movement of the x-ray C-arm 4, its orbital panning then ensues around a rotation axis (not shown) tilted corresponding to the longitudinal axis 22.

An x-ray source 34 and an image intensifier 36 are mounted on the two ends of the C-arm segment 126. The x-ray source 34 and the image intensifier 36 together form an imaging system whose center ray 38 likewise runs through the isocenter 32. It is thus ensured that the center ray 38 pierces the isocenter 32 in every angular and orbital position of the C-arm segment 16.

The C-arm segment 16 is shown in its base position in FIG. 1, meaning that the center ray 38 propagates in the perpendicular direction. By orbital movement of the C-arm segment 16 in direction 20 (as, for example, shown in FIG. 2), the center ray 38 moves as well so as to span an orbital plane 40 that contains the center ray 38 and the pivot axis 26. For clarity, only a small portion of the orbital plane 40 in FIG. 1 hatched, but it extends beyond the hatched region and the diameter of the x-ray C-arm 4.

On its side 42 situated radially outwards, the therapy C-arm 8 is supported on a guide 44. A support 46 (not shown) corresponding to the support 18 is present in the guide 44 for this purpose, on which support 46 the therapy C-arm 8 can move orbitally in the direction of the arrow 48. With its end 50, the guide is supported on the bearing block 52 of a base body 54. A non-visible joint 56 is arranged between the bearing block 52 and the guide 44, which allows a rotation around an axis 58 parallel to the longitudinal axis 22.

As an alternative or in addition to the shown embodiment, guide rails (not shown in Figures) with corresponding sled can also be attached on the base body 54 or bearing block 52 and on the guide 44, on which guide rails the therapy C-arm 8 can be shifted away from the patient region together with the guide 44, for example parallel to the axis 26. Other arrangements of rails are also conceivable, such that the x-ray C-arm 4 together with the shockwave head 6 can move two-dimensionally within certain limits.

A sled 62 is supported on the radially-inwards side 60 of the therapy C-arm 8 such that said sled 62 can likewise move orbitally in direction 48. A boom 64 is attached on the sled 62 with its fixed end 67, the boom 64 pointing in the direction towards the x-ray C-arm 4 and supporting the shockwave head 6 on its free end 66. For orbital movement of the shock head 6, sled 62 on the therapy C-arm 8 and therapy C-arm 8 on the guide 44 are simultaneously moved, for example via a chain drive (not visible in FIG. 1) arranged inside the therapy C-arm 8. The fact that the two movements just cited are thereby no longer independent of one another is irrelevant for the functionality of the system 2. The orbital movements of therapy C-arm 8 and sled 62 likewise ensue around the longitudinal axis 22.

The entire therapy C-arm 8 with its base body 54 is displaced at an axial separation from the x-ray C-arm 4 or parallel to the orbital plane 40, meaning that the plane that the therapy C-arm 8 spans lies parallel to the orbital plane 40 and separated therefrom. The boom 64 extends in the direction towards the x-ray C-arm 5 so far that the shockwave head 6 attached on it in turn lies in the orbital plane 40. The distance is measured such that a focus point 70 of an ultrasonic shockwave emitted by the shockwave head 6 and represented in FIG. 1 by the cone 72 lies in the orbital plane 40. The cone tip forms the focus point 70 and lies in the isocenter 32. The shockwave head 6 is an ultrasound shockwave head for generation of an ultrasonic pulse focused in the focus point 70.

The shock axis 68, thus the propagation direction of the ultrasonic pulse, passes through the focus point 70, lies in the orbital plane 40 and coincides with the center ray 38 in FIG. 1. For this reason FIG. 1 represents a type of arrangement known as an inline position of shockwave head 6 and x-ray system 34, 36. Due to an x-ray-transparent zone 96 (visible in FIG. 2) surrounding the shock axis 68 in the shockwave head 6, during the shockwave treatment of a patient 76 a simultaneous x-ray positioning of the subject to be treated or an exposure of the surroundings of the focus point 70 inside the patient body can in fact occur. The x-rays emitted from the x-ray source 34 can penetrate the x-ray-transparent zone 96 of the shockwave head 6 along the center ray 38. At the same time the shockwave head 6 is positioned on the stomach-side of the patient in order, for example, to treat a stone in the ureter of the patient. This is known as the over-table treatment position.

Due to the coaxial arrangement of x-ray C-arm 4 and therapy arc 8, the position of the focus point 70 is maintained in the isocenter 32 in every travel position of the shockwave head 6. The shock axis 68 always lies in the orbital plane 40.

The exact geometric alignment of articulated arm 8 and x-ray C-arm 4 relative to one another ensues in that the base body 14 and the base body 54 are mounted on common foot part 74. The alignment is effected at the factory in the manufacture of the SWL system 2.

The treatment point of the SWL system 2 represented by the focus point 70 always lies in the isocenter 32. In an imaging phase of the treatment of the patient 76 he, with his point to be treated, is therefore brought into the isocenter 32 (already occurred in FIG. 1). In order to non-invasively locate the point to be treated inside the patient 76, the imaging system (x-ray source 34 and image intensifier 36) supplies x-ray exposures that are shown on screens 82 of the display module 12. Due to the flexible, weight-compensating carrier arm 84, the screen 82 can be moved into an advantageous observation position for the operating personnel of the system 2. In order to three-dimensionally position the treatment point, at least two x-ray images of the patient 76 are created (possibly given a shockwave head 7 that is initially pivoted away) by moving the x-ray C-arm 4 around the axis 22 (orbital positioning) or 26 (angular positioning), for example between the positions shown in FIG. 1 and FIG. 2. For movement of the patient 76, a recumbent surface 78 on which the patient 76 rests is one end on a permanently-installed base and can be moved linearly in all spatial directions 90.

The direction of the shockwave head 6 towards the patient 76 can ensue in two manners. One way is for the treatment position of the patient 76 to be sought first and then marked, for example electronically stored given a recumbent surface that can be moved via motors. The recumbent surface 78 together with the patient 76 is subsequently moved a bit so that the shockwave head 6 can be moved into the position shown in FIG. 1; the patient 76 is then moved towards the shockwave head 8 from below until the treatment position stored above is reached again. The position shown in FIG. 1 is thus reached.

Alternatively, due to the entire therapy C-arm 8 that can be moved around the axis 58, the coupling of the shockwave head 6 can ensue on the patient 76 brought into the treatment position (and henceforth recumbent), with the therapy C-arm 8 that was previously pivoted upwards being lowered together with the shockwave head 6 onto the abdomen (facing upwards) of the patient 76. This coupling variant applies in particular for the embodiment of the SWL system 2 according to FIG. 4 through FIG. 6.

If the shockwave head 6 is coupled on the patient 76, the treatment can begin by activation of the ultrasonic shockwaves.

When it is not directly needed, the entire x-ray C-arm 4 can be pivoted away from the patient region (not shown in Figures) on a further rotation axis 86 that passes perpendicularly through the base body 14 and the foot part 74, which increases the access for the treatment personnel at the patient 76. The pivoting ensues from the base position shown in FIG. 1 in the direction of the arrow 88.

"Wandering" or unwanted movement of the shockwave head 6 (due to its dead weight and the contact pressure on the patient and the deformation of the therapy C-arm 8) can be corrected by a slight rotation of the therapy C-arm 8 around the axis 58.

Figure 2:
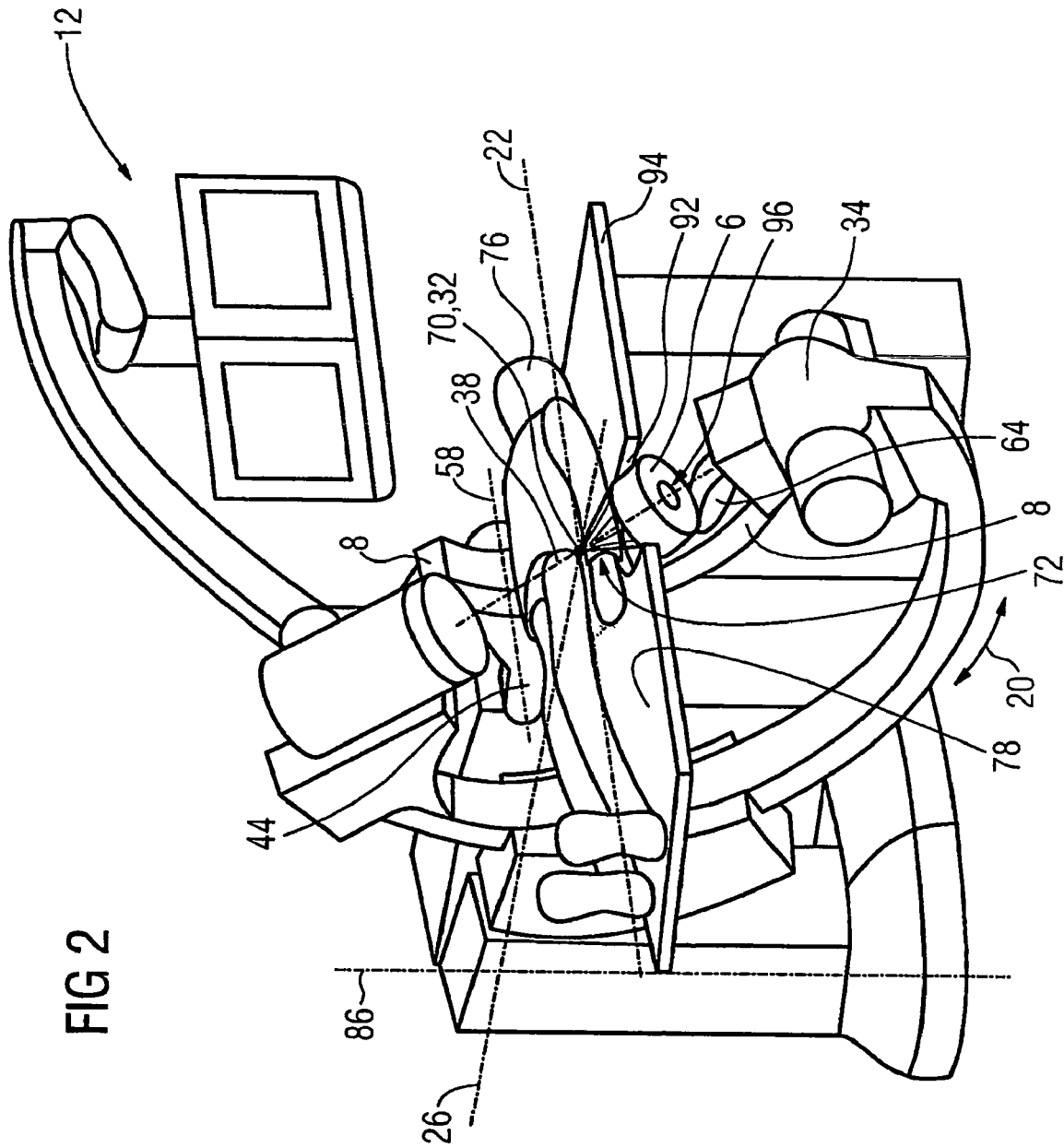
FIG. 2 shows the system from FIG. 1 with shockwave head in an under-table treatment position for the left (machine-remote) patient side, with the x-ray system orbitally panned into inline position.

The treatment position shown in FIG. 2 (known as the under-table left position) treats, for example, the left kidney of the patient 76. The shockwave head 6 is moved into the under-table position. Relative to FIG. 1, the sled 62 (covered in FIG. 2 by the x-ray source 34) is moved to the opposite end of the therapy C-arm 8. The therapy C-arm 8 itself is additionally moved in its guide 44 to the opposite end relative to FIG. 1. The shockwave head 6 protrudes into a recess 92 of the recumbent surface 78 in order to be brought optimally close to direct contact on the patient 76. The cone 72 of the ultrasonic rays generated by the shockwave head 6 hereby penetrate a water-filled coupling bellows (not shown) which is coupled between shockwave head 6 and patient 76 with an intermediate layer of gel and furthermore with the body tissue of the patient insofar as that the focus point 70 strikes a kidney stone (not shown) in the body of the patient 76.

As in FIG. 1, the x-ray C-arm is located in base position with regard to the axis 26. However, it is pivoted counter-clockwise by approximately 40 degrees in direction 20 in order to expose the patient 76 at an angle. The 40 degree position is a typical position for treatment of kidney stones.

In FIG. 2 it can be seen that the shockwave head 6 on the boom 64 is eccentrically mounted, namely on the side of the boom 64 facing away from the system in the under-table position. In the direction of the front side 94 of the recumbent surface, the shockwave head 6 hereby stands further removed from the patient table 10 than the therapy C-arm 8 and the boom 64. The doctor normally standing next to the patient table 10 on the front side 94 that is limited as little as possible in his legroom or, respectively, freedom of movement. Since, in the upper-table position, the 180 degree position of the shockwave head 6 shown in FIG. 1 is the most extreme position of the shockwave head 6, here the projection of therapy C-arm 8 and boom 64 is also bearable for the treating doctor in his head region. A further possibility to make the C-arm smaller is moreover hereby provided.

The central x-ray-transparent zone 96 in the shockwave head 6 is visible in FIG. 2, which x-ray-transparent zone 96 serves for inline positioning in the shockwave treatment. Due to the stationary resting isocenter 32, the recumbent surface 78 is somewhat raised relative to FIG. 1 and displaced towards the right patient side in order to place the patient's left kidney in the treatment point (thus the isocenter 32) instead of the ureter.

Figure 3:
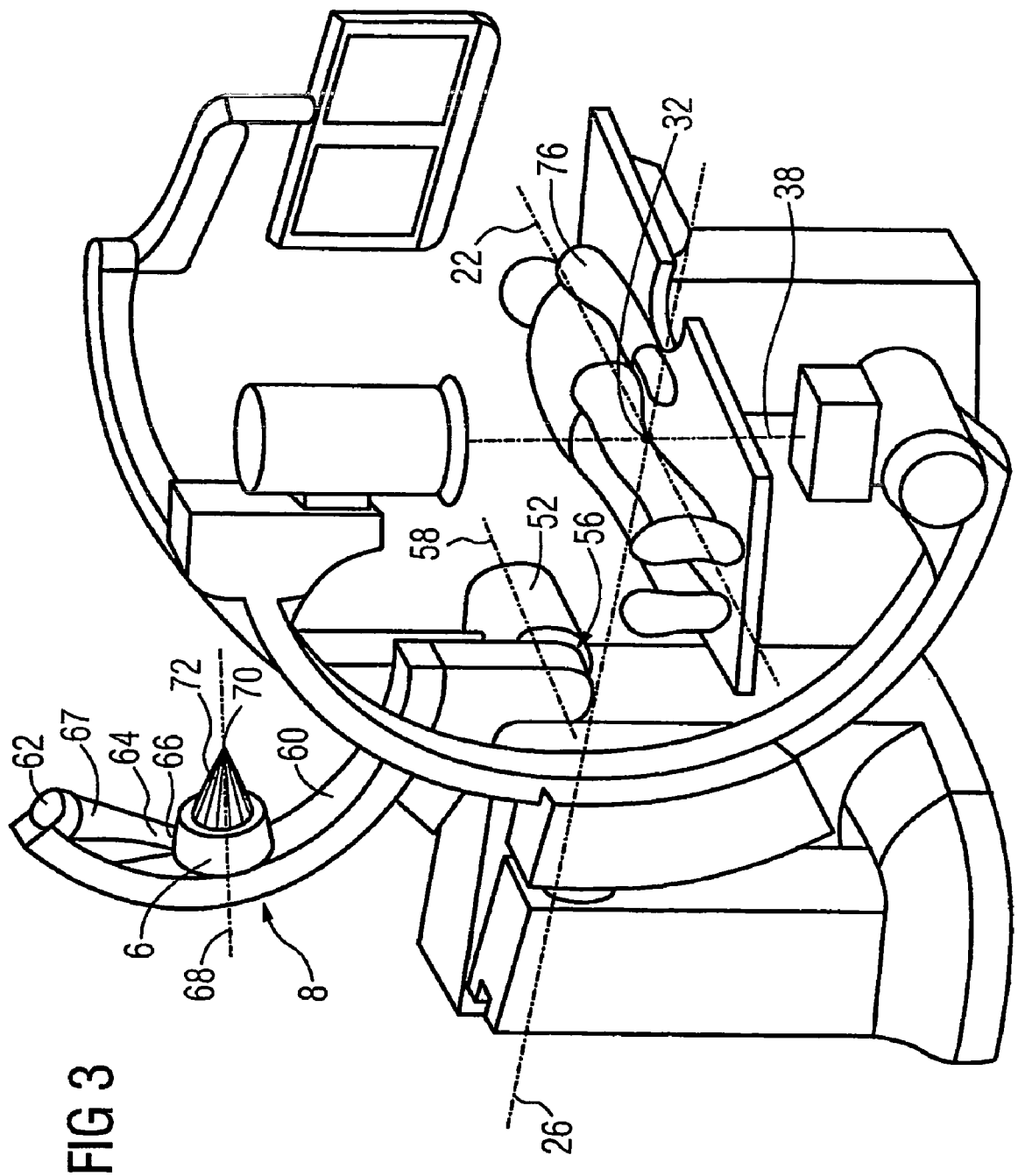
FIG. 3 shows the system from FIG. 1 with the therapy C-arm and the shockwave head in a park position.

FIG. 3 shows the therapy C-arm 8 in park position. The entire therapy C-arm 8, together with the shockwave head 6, is pivoted upwards by approximately 90 degrees around the axis 58 from the position shown in FIG. 1. The entire patient torso region is free, which makes the access to the patient 76 distinctly easier for treatment personnel. This is advantageous in an emergency situation or given the treatment preparation or follow-up.

Figure 4:
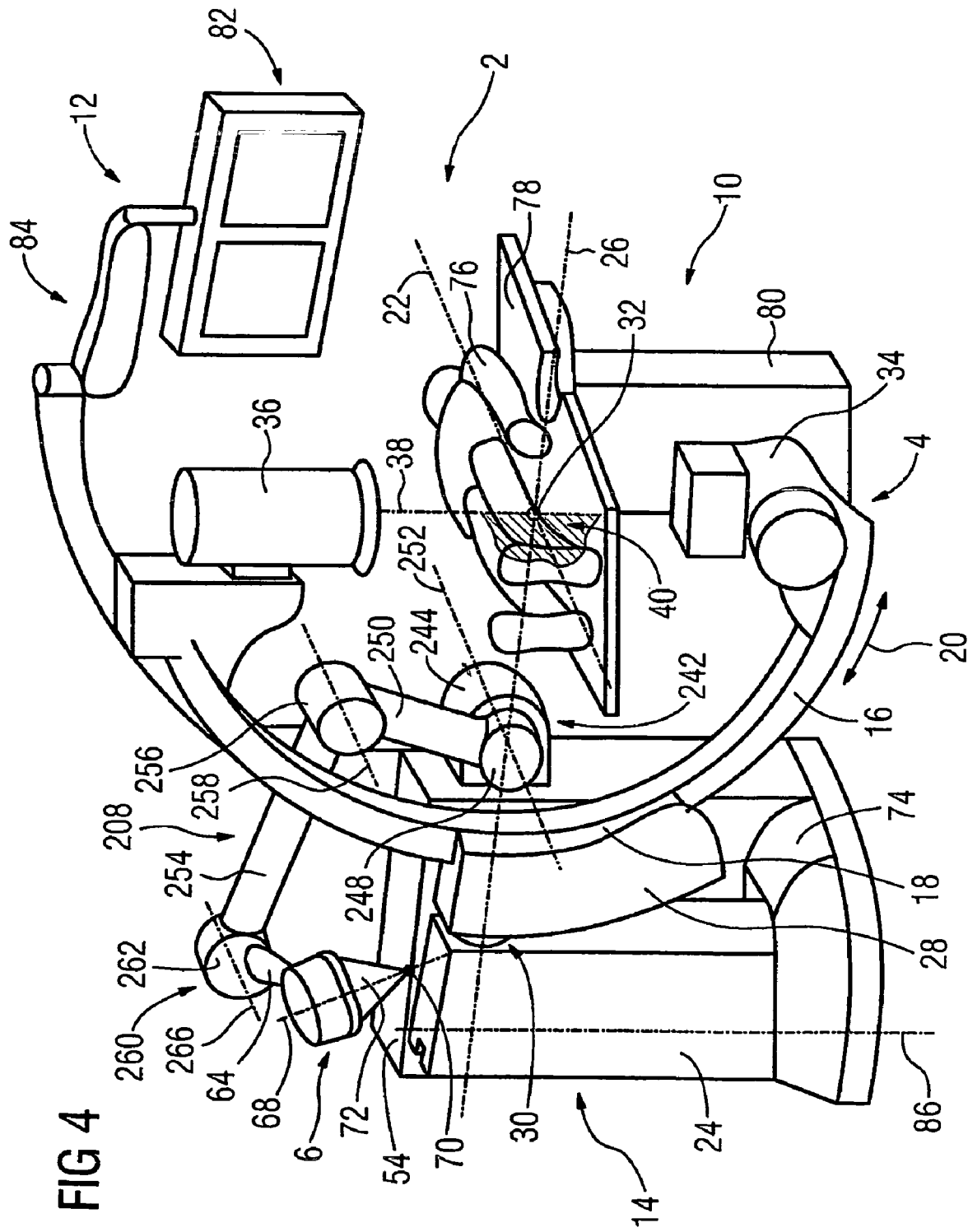
FIG. 4 shows the shockwave lithotripsy (SWL) system in a second embodiment with an articulated arm and the shockwave head in a park position and the x-ray C-arm in a base position.

FIG. 4 shows the SWL system 2 in an alternative embodiment, namely with an articulated arm 208 as a carrier device.

The articulated arm 208 is borne with its one end 242 on the bearing block 244 of the base body 54. A joint 248 is arranged between a bearing block 244 and an arm segment 250, the joint 248 allowing a rotation on an axis parallel to the longitudinal axis 22. A further joint 256 which can be pivoted on an axis 258 likewise running parallel to the longitudinal axis 22 is attached between the arm segment 250 and a further arm segment 254. A further joint 262 is attached at the free end 260 of the articulated arm 208, the joint 262 connecting the arm segment 254 with the boom 64 and allowing rotation (together with the shock head 6) on the axis 266 likewise proceeding parallel to the longitudinal axis 22.

The entire articulated arm 208 with its base body 46 is offset by an axial distance from the x-ray C-arm 4 or parallel to the orbital plane 40, meaning that the longitudinal axes of the arm segments 250 and 254 proceed parallel to the orbital plane 40. The boom 64 extends in the direction of the x-ray C-arm 4 so far that the shock head 6 attached on it in turn lies in the orbital plane 40. The separation is measured such that the focus point 70 of the ultrasonic shockwave (represented in FIG. 4 by the cone 72) emitted by shock head 6 lies in the orbital plane 40. The shock axis 68 again passes through the focus point 70 and lies in the orbital plane 40.

Due to the parallelism of all axes 252, 258 and 266 around which the individual parts of the articulated arm 208 can be pivoted, the focus point 70 can only be displaced two-dimensionally and in fact always within a region of the orbital plane 40 demarcated by the dimensions of the articulated arm 208. The focus point 70 can be directed towards the isocenter 32 by pivoting of the articulated arm 208.

In FIG. 4 the articulated arm 208 and the shockwave head 6 are moved into what is known as a park (standby) position, i.e. moved as far as possible from the surrounding region of the patient 76 resting on the patient table 10. The access to the patient 76 from all sides is thus possible without hindrance for treatment personnel or, respectively, doctors (not shown). For example, in the situation shown in FIG. 4 an imaging phase can ensue before or after the treatment of the patient 76. The ultrasound cone 72 and the focus point 70 are in fact shown in FIG. 4, but the ultrasound source is normally deactivated.

If the body region of the patient 76 to be treated lies in the isocenter 32, the shock head 6 is directed towards the patient by pivoting the articulated arm 208. The patient does not have to be repositioned for this purpose. The x-ray C-arm 2 is temporarily tilted on the pivot axis 26 out of its angular base position shown in FIG. 4 in order to avoid a collision. If the focus point 70 is brought into the isocenter 32, the treatment can be begun via activation of the ultrasonic shockwave.

Figure 5:
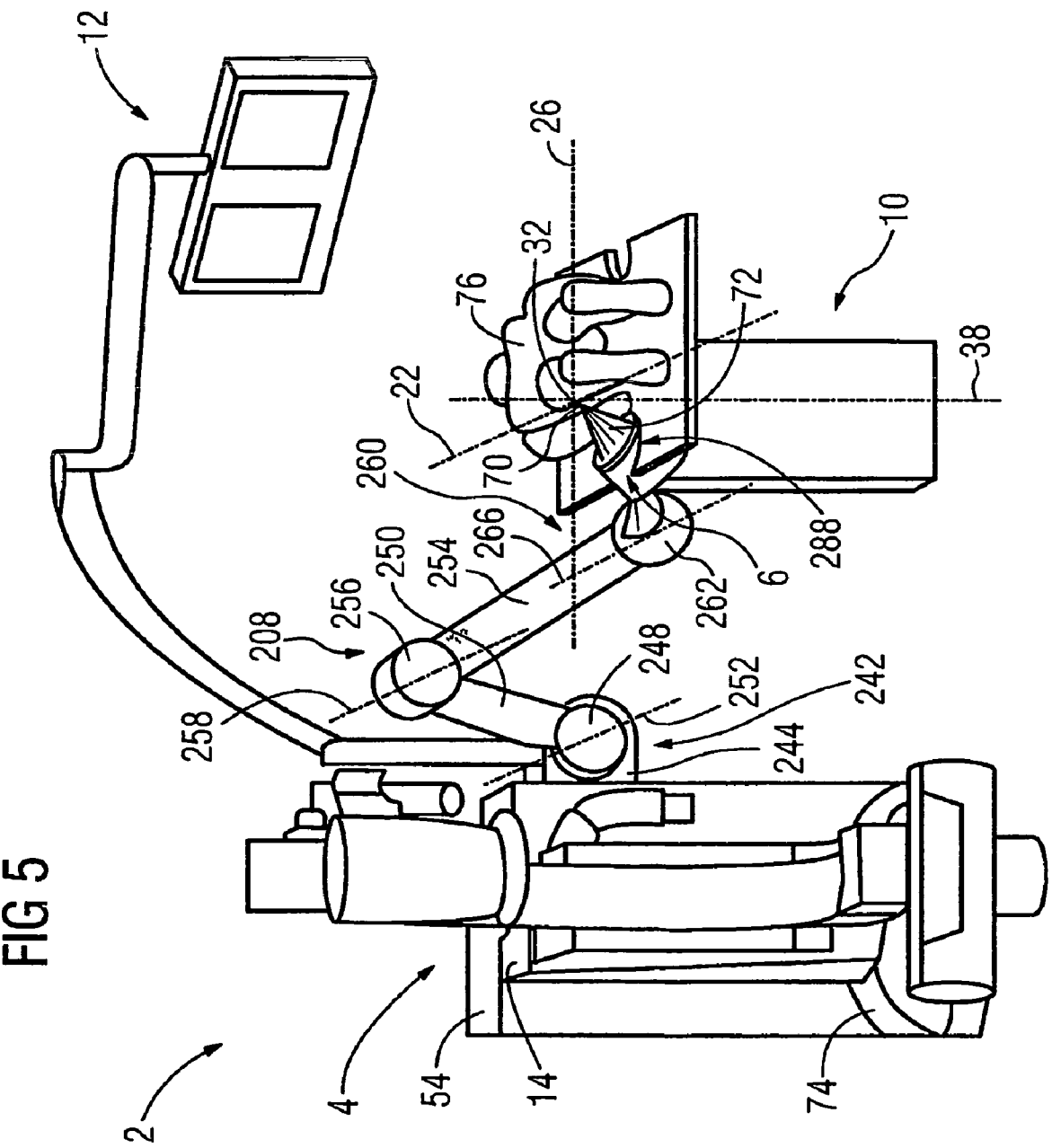
FIG. 5 shows the SWL system of FIG. 4 with a parked (thus swiveled-out) x-ray C-arm and the shockwave head in a treatment position (under-table—right).

The entire x-ray C-arm 4 can be pivoted out of the patient region on the rotation axis 86 that crosses perpendicular to the base body 14 and the foot part 74, which enables the unlimited access to the patient 76 for the treatment personnel. This park position of the x-ray C-arm 4 is shown in FIG. 5. Instead of this the articulated arm 208 is moved into a treatment position in which the focus point 70 coincides with the isocenter 32. The right kidney can thus be treated from approximately the 40° position at the back of the patient 76; this is what is known as the under-table right position.

Angle sensors (not shown) that detect the respective rotation position of the appertaining joint and forward it to a central computer (not shown) are present in the joints 248, 256 and 262. The respective positions of the arm segments 250 and 252 or of the shockwave head 6 and thus of the focus point 70 can be determined in a suitable manner in the central computer from the known dimensions of the entire articulated arm 208 via detection of the rotation angle of the joints 248, 256 and 262. This central computer controls the motors (likewise not shown) in the joints 248, 256 and 262 such that the focus point 70 comes to lie exactly in the isocenter 32. An automated control of the entire articulated arm 208 or, respectively, its movement is thus enabled.

Due to the x-ray C-arm 4 being moved away, the longitudinal axis 22, pivot axis 26 and center ray 38 from FIG. 4 are again plotted dashed. Due to the space-saving arrangement of the articulated arm 208 on only one side of the patient 76 (namely the right, which is also the treatment side in FIG. 5), the access to the patient is enabled with the largest possible free space. The shock head 6 protrudes into a recess 288 (opposite the recess 92) of the recumbent surface 78 in order to be brought optimally close to direct contact on the patient 76.

The x-ray C-arm 4 can pivot on the rotation axis 86 parallel to the orbital plane 40 and perpendicular to the rotation axes 252, 258 and 266. Since the rotation axes 252, 258 and 266 typically proceed horizontally, the orbital plane 40 stands vertically; the rotation axis 86 for the x-ray C-arm 2 likewise stands vertically. The x-ray C-arm 2 can thus be moved away from the treatment area in the manner of the movement of a door when it is not required. In spite of the x-ray C-arm 4 being pivoted away, the treatment of the patient 76 with the shockwave head 6 remains spatially precise since its spatial position relative to the SWL system 2 does not change.

In such a position of the SWL system 2 an inline ultrasound positioning is then possible. The access to the patient 76 is then namely also possible from the back side of the patient table 10 facing towards the machine. The back side of the shockwave head 6 is freely accessible via the articulated arm 208 displaced towards the head end of the patient 76. An ultrasound applicator (not shown) can thus be inserted into a central opening (not shown) in the shockwave head 6 and an ultrasound positioning of the subject to be treated in the patient body can hereby be implemented. The central opening can be arranged in the region of the x-ray-transparent zone 96.

Figure 6:
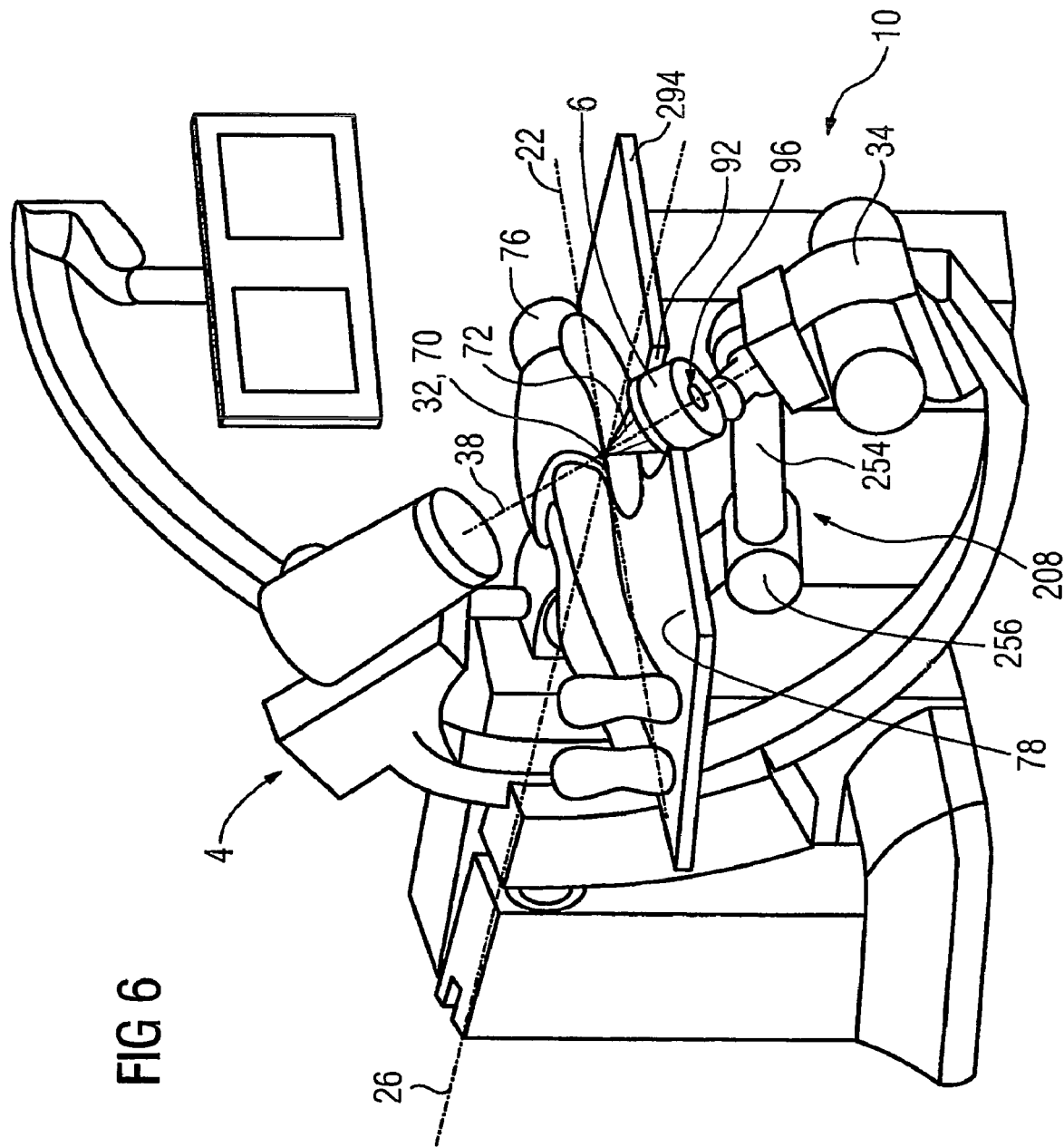
FIG. 6 shows the system of FIG. 4 with the shockwave head in a treatment position (under-table—left) and a tilted x-ray C-arm in the inline position.

FIG. 6 shows an operating situation of the system 2 in which an x-ray radioscopy with the aid of the x-ray C-arm 4 ensues simultaneously with the shockwave treatment of the patient 76 with the aid of the x-ray C-arm 4. The shockwave head 6 is located in the inline position. The x-rays emitted from the x-ray source 34 can penetrate through the x-ray-transparent zone 96 along the center ray 38 of the shockwave head 6. At the same time the shockwave head 6 is positioned on the left patient side corresponding to FIG. 5 (thus in approximately the −40° position) in order, for example, to treat a kidney stone of the left kidney of the patient (under-table left position as in FIG. 2). Due to the stationary resting isocenter 32, the recumbent surface 79 is displaced relative to FIG. 5 by approximately the distance of the kidney of the patient to be treated from the right patient side. The focus point 70 again coincides with the isocenter 32. The x-ray arrangement 76 is tilted on the longitudinal axis 22 in order to irradiate the patient 76 at an angle. The recess 96 in the recumbent surface 78 in turn offers space for the shockwave head 6.

From FIG. 6 it is clear that, although the shock head 6 is located on the apparatus-remote side of the patient table 10, this barely protrudes over the apparatus-remote table edge 294 and thus gives the treating doctor sufficient legroom, and therewith furthermore allows the greatest possible patient access. In contrast to the first embodiment, given an articulated arm 208 as a carrier device no further component (outside of the shockwave head 6) is also disruptively present in the head or foot region of the doctor in the over-table position (not shown in Figures).

If patient 76 and recumbent surface 78 are located in a lateral middle position between the positions shown in FIGS. 5 and 6, the third significant possibility (not shown in Figures) to treat the patient 76 is present. Given a patient position lowered somewhat relative to FIGS. 5 and 6, the shock head 6 can be moved into over-table position in order to treat the patient 76 from above; thus treat the abdomen side of said patient centrally in the ureter region. The shockwave head 76 would then (for example in FIG. 4) be arranged on the top of the abdomen of the patient 76 between this and the image intensifier 36, such that at the same time an x-ray radioscopy (inline) of the patient 76 can again occur. Here as well no component of the system 2 protrudes beyond the table edge 294 towards the machine-remote side on which the doctor stays. Starting from the position in FIG. 3, this can ensue via tilting of the arm segment 254 on the axis 258 and tilting of the shock head 6 on the axis 266.

Although modifications and changes may be suggested by those skilled in the art, it is the invention of the inventors to embody within the patent warranted heron all changes and modifications as reasonably and properly come within the scope of their contribution to the art.

The invention claimed is:

1. A system for image-supported shockwave treatment, comprising:
   a base support;
   a patient table adapted to receive a patient thereon;
   an x-ray C-arm mounted to said base support, said x-ray C-arm, in a base position relative to said base support, spanning and thus defining an orbital plane, said C-arm being movable orbitally in said orbital plane around an isocenter, said x-ray x-ray C-arm having an x-ray source and a radiation detector mounted thereon to obtain x-ray images of an examination subject on the patient table;
   a therapy device comprising a therapy C-arm on which a shockwave head is mounted that emits focused shockwaves adapted to interact with an examination subject on the patient table;
   said therapy C-arm being mounted to said base support laterally from, and stationary relative to, said x-ray C-arm with said therapy C-arm parallel to and spaced from said orbital plane of said x-ray C-arm, and being orbitally movable;
   a boom having a fixed end connected to said therapy C-arm and a free end at which said shockwave head is attached; and
   said boom being orbitally movable by and slidably movable within said therapy C-arm to arbitrarily position said shockwave head in said orbital plane within an angle range of at least 180° above and below the patient table, and aligned to said isocenter.

2. A system as claimed in claim 1 wherein said therapy C-arm moves said boom in a plane parallel to said orbital plane of said x-ray C-arm.

3. A system as claimed in claim 1 wherein said shockwave head comprises a central region therein, extending along a shockwave axis of the shockwave head, which is permeable for x-rays.

4. A system as claimed in claim 1 wherein said x-ray C-arm is mounted to said base support for angular movement of said x-ray C-arm.

5. A system as claimed in claim 1 wherein said therapy C-arm and said boom and said shockwave head are movable between a treatment position, at which said shockwave head is located above or below a patient on the patient table, and a park position at which said shockwave head is remote from said patient table.

6. A system as claimed in claim 1 wherein said patient table proceeds through said x-ray C-arm, and wherein said patient table comprises a table support disposed outside of a movement range of said x-ray C-arm and a movement range of said therapy C-arm.

* * * * *